United States Patent [19]

Schapira et al.

[11] Patent Number: 5,021,083

[45] Date of Patent: Jun. 4, 1991

[54] STABLE AQUEOUS OR AQUEOUS ALCOHOLIC DISPERSION BASED ON DERIVATIVES OF OXYNIL, HERBICIDAL COMPOSITION COMPRISED THEREOF AND SELECTIVE HERBICIDAL TREATMENT COMPRISING THE USE OF THE SAID HERBICIDAL COMPOSITION

[75] Inventors: Joseph Schapira, Paris; Jacques Pecheur, Colombes; Jacques Vincent, Mareil Marly; Jacques Schild, Gennevilliers; Bruno Bosselin, Chelles, all of France

[73] Assignee: Compagnie Francaise De Produits Industriels, Gennevilliers, France

[21] Appl. No.: 228,899

[22] Filed: Aug. 5, 1988

[30] Foreign Application Priority Data

Aug. 6, 1987 [FR] France ................................ 8711230

[51] Int. Cl.⁵ ..................... A01N 33/00; A01N 43/66

[52] U.S. Cl. ........................................ 71/105; 71/93; 71/65; 71/79

[58] Field of Search .................................. 71/93, 105

[56] References Cited

FOREIGN PATENT DOCUMENTS

| 0064478 | 11/1982 | European Pat. Off. . |
| 1408238 | 7/1965 | France . |
| 1442294 | 5/1966 | France . |
| 2332053 | 6/1977 | France . |
| 2126897 | 4/1984 | United Kingdom . |

*Primary Examiner*—David B. Springer
*Attorney, Agent, or Firm*—Fleit, Jacobson, Cohn, Price, Holman & Stern

[57] ABSTRACT

Stable aqueous or aqueous alcoholic dispersion, or aqueous flow, based on at least one oxynil derivative, wherein the oxynil derivative is an ester of melting point higher than 65° C. and herbicidal composition comprising the said dispersion.

11 Claims, No Drawings

STABLE AQUEOUS OR AQUEOUS ALCOHOLIC DISPERSION BASED ON DERIVATIVES OF OXYNIL, HERBICIDAL COMPOSITION COMPRISED THEREOF AND SELECTIVE HERBICIDAL TREATMENT COMPRISING THE USE OF THE SAID HERBICIDAL COMPOSITION

The invention relates to a stable aqueous or aqueous alcoholic dispersion based on oxynil derivatives as well as a herbicidal composition comprised thereof, the generic term oxynil denoting ioxynil and bromoxynil which constitute well-known herbicides.

The invention also relates to a selective herbicidal treatment comprising the use of the abovesaid herbicidal composition.

Bromoxynil is the common name of 3,5-dibromo-4-hydroxybenzonitrile and ioxynil that of 3,5-diiodo-4-hydroxybenzonitrile.

It is by the term of "aqueous flow" term which is established and accepted in the art that are designated stable aqueous or aqueous alcoholic dispersions of substances particularly herbicides in the solid state of a granulometry substantially less than about 5 μm; these dispersions are stabilized by means of surface-active agents, dispersing substances and thickening products and/or protective colloids which confer on them a good fluidity whilst retarding sedimentation to the maximum.

The dispersion is called an aqueous alcoholic dispersion when it contains one or several alcohols of the glycol type, for example ethyleneglycol, propyleneglycol and butoxyethanol, the proportion of these glycols in the dispersion ranging from 1 to 10% by weight, preferably from 3 to 7%.

In practice, the flows must be stable during periods ranging up to two years: their constitution is similar to that of paints.

There already exist flows based on bromoxynil-phenol.

However, oxynils in the phenol form are less active from the herbicidal point of view than when they are employed in ester form, at equal doses of active material to the hectare, expressed as phenol equivalent (p.e.).

This is the reason why the technician skilled in the art prefers a priori to resort to oxynil esters—particularly to octanoates and to octanoate/butyrate associations—since the latter, due to the fact of their greater activity, necessitate application doses expressed in active material equivalent to the hectare which are lower.

However, this greater activity results frequently in problems of phytotoxicity with respect to the crop concerned.

And, moreover, the use of esters of technical grade, i.e. not purified—in the present specification, the esters when mentioned are always of technical grade—in flow form has never been envisageable by reason of the fact that, while all the oxynil esters respond well to the first of the three conditions specified below—and which all three must be satisified so that a given active material may be put into flow form—, the majority of them do not respond simultaneously to the two others, said conditions being that the active material concerned is insoluble in an aqueous or aqueous alcoholic medium,
shows a sufficiently high melting point to permit grinding to a granulometry substantially less than about 5 μm and,
does not show a tendency to hydrolysis in the presence of water.

In fact, the relatively long chain esters and particularly the octanoate which is the ester most used, show too low a melting point to be brought by grinding to the granulometry indicated above whereas the majority of those with a relatively short chain provide proof of a certain tendency to hydrolysis in the presence of water, such hydrolysis being therefore to be expected in the course of their formulation in flow form.

Applicants have had the merit to overcome this situation and to find that it was possible to prepare a flow based on oxynil ester when the melting point of this ester is higher than 65° C.

And their merit has been all the greater as, unexpectedly, the oxynil ester, under the form of the thus constituted flow, not only shows a herbicidal activity close to that which it shows in its most effective conventional form—namely that of an emulsifiable concentrate in which it is solubilized—but also and above all is much less phytotoxic than this most effective conventional form, particularly in the case of its use on maize crops, vineyards, orchards, straw cereals, meadow gramineae, vegetable crops and leguminous plants.

The flow thus established therefore constitutes a novel industrial product.

Consequently, the stable aqueous or aqueous alcoholic dispersion or aqueous flow based on at least one oxynil derivative according to the invention is characterized by the fact that the oxynil derivative is constituted by an ester of melting point higher than 65° C.

And the herbicidal composition according to the invention is characterized by the fact that it comprises a stable aqueous or aqueous alcoholic dispersion or aqueous flow based on an oxynil ester of melting point higher than 65° C.

Furthermore, the selective herbicidal treatment of crops of the group comprising maize or corn, vineyards, orchards, straw cereals, meadow gramineae, vegetable crops and leguminous plants, is characterized by the fact that the said crops are treated by way of an efficient amount of the said herbicidal composition.

According to an advantageous embodiment, the herbicidal composition according to the invention comprises in addition a flow based on one or several triazines and/or substituted ureas and/or amides and/or diphenylethers and/or derivatives of benzoic acid and/or picolinic derivatives.

According to another advantageous embodiment, the herbicidal composition according to the invention comprises, besides the flow based on oxynil ester and possibly besides the other flows mentioned above, another herbicide in the form of an aqueous solution provided that this aqueous solution does not exert any solubilizing hydrotropic effect on the oxynil ester, particularly an aqueous aminotriazole solution and/or an aqueous solution of glyphosate.

The invention envisages also other features which will be more explicitly considered below.

And it will be well understood by means of the additional description which follows and of the examples which are not limiting but which relate to advantageous embodiments.

Proposing, consequently, to establish the aqueous flow as well as the herbicidal composition according to the invention, procedure is as follows or in equivalent manner.

Firstly an oxynil ester is selected of melting point higher than 65° C., as well as the adjuvants—that is to say the surface-active agents, the dispersing products and the thickening products and/or the protective colloids—necessary for ensuring the stability of the flow based on oxynil ester.

Among the oxynil esters which are suitable, are to be mentioned those of the group comprising the acetate, propionate, butyrate, isobutyrate and pivalate of bromoxynil whose melting points, when they are of technical grade, are respectively 154° C., 115° C., 82° C., 103° C. and 118° C.

the acetate, propionate, butyrate, isobutyrate and pivalate of ioxynil whose melting points, when they are of technical grade, are respectively 204° C., 157° C., 118° C., 138° C. and 142° C.

The butyrates of bromoxynil and of ioxynil are particularly preferred.

The triazines which may be suitable are selected from the group comprising atrazine, simazine, metribuzine, cyanazine, terbutryne and terbuthylazine; the substituted ureas may be selected from the group comprising chlortoluron, isoproturon, diuron, neburon and methabenzthiazuron.

The amides which may be suitable may be selected from the group comprising metolachlore, metazachlore, diflufenican and isoxaben.

As diphenylethers which are usable, may be mentioned bifenox and chlomethoxynil, as derivatives of benzoic acid, may be mentioned 2-methoxy-3.6-dichlorobenzoic acid or dicamba and, as picolonic derivatives, may be mentioned 3.6-dichloropicolinic acid known under the name of clopyralide.

Among the surface-active agents which can be suitable, are mentioned those of the group comprising:

non-ionic surface-active agents and more particularly
polyethoxylated fatty alcohols, polyethoxylated castor oils, polyethoxylated alkylphenols such as nonylphenol condensed on the average with 10 moles of ethylene oxide and polyethoxylated polyarylphenols such as tristyrylphenol condensed on the average with 18 moles of ethylene oxide, and/or anionic surface-active agents such as sulphated and/or phosphated derivatives of the preceding non-ionic agents, possibly neutralized in the form of alkali or alkanolamine salts as well as the alkylsulfosuccinates such as dioctylsulfosuccinate and diisobutylsulfosuccinate of alkali metals.

Among the dispersant products which can be suitable, will be mentioned those of the group comprising the polynaphthylmethanepolysulfonates of sodium, potassium, ammonium and/or alkanolamine, poly(alkylnaphthylmethane)-polysulfonates of alkali metals, ammonia and/or alkanolamine, and the latter can contain a certain proportion of monomer; it is also possible to resort to polycarboxylic dispersing agents such as polymers of acrylic acid and/or of maleic anhydride and of their derivatives.

Among the thickeners and/or protective colloids which can be suitable, will be mentioned laponites, attapulgites, bentonites, treated if necessary, and polymers of ethylene oxide of high molecular weight, such as POLYOX ® and heteropolysaccharides obtained by fermentation of Xanthomonas Campestris like RHODOPOL ® 23 manufactured by Rhone-Poulenc or KELZAN S ® of the Kelco Company.

Once the one or more esters and adjuvants have been selected, the one or more abovesaid esters are melted and they are dispersed in the presence of one or several surface-active agents with vigorous shaking in water, advantageously hot, which can contain the other adjuvants.

Regarding the stabilizing adjuvants, their dose in per cent by weight on the final formulation is for the surfactants used alone or associated with each other, comprised between 0.1% and 15% by weight, for the dispersing agents used alone or in association, between 0.5% and 15% by weight, for the thickeners or protective colloids, between 1 per 100,000 and 1 per 100 by weight, generally between 1 per 10,000 and 1 per 1,000 according to the products employed.

The dispersion so obtained is ground so as to bring the granulometry of the oxynil ester substantially to a value less than 5 μm.

Then advantageously an effective proportion of antifoaming product such as dimethylpolysiloxane is added.

The dispersion so obtained is de-aerated under vacuum and filtered in order to remove possible lumps.

The resulting product constitutes the desired flow.

This flow is, if necessary, combined with a stable aqueous dispersion or flow of triazine and/or of substituted urea and/or of diphenylether and/or of amide and/or an aqueous solution of the salt of benzoic acid and/or of picolinic derivative and/or of aminotriazole.

The ratios by weight between these various active materials may be fixed between 1 and 25 according to the substances concerned and the contents of active materials are selected between 25 and 500 g/l of oxynil equivalent, introduced in the form of ester and presented in flow form, between 50 and 450 g/l for triazines in flow form, between 50 and 450 g/l for substituted ureas in flow form, between 50 and 250 g/l for diphenylethers in flow form, between 50 and 600 g/l for amides in flow form, between 100 and 200 g/l for salts of benzoic acid in the form of aqueous solution, between 10 and 200 g/l for picolinic derivatives in the form of aqueous solution, between 20 and 150 g/l for aminotriazole.

The overall content of the final herbicidal composition in its various active substances does not generally exceed 600 g/l.

The stable dispersions or flows based on one or several triazines and/or based on substituted ureas and/or amides and/or diphenylethers and/or derivatives of benzoic acid and/or picolinic derivatives and/or aminotriazoles, are prepared in the manner indicated above with regard to flows of oxynil ester with the exception of the initial melting step since these products are already in powder form.

The details relating to the preparation and to the constitution of the herbicidal compositions according to the invention will be evident from the examples 1 to 34 which follow.

EXAMPLE 1

42.8 parts by weight of technical grade bromoxynil butyrate (melting point 82° C., content of bromoxynil equivalent 74.8%) and 2 parts by weight of nonylphenol (polyethoxylated on the average with 10 moles of ethylene oxide) are melted together and poured with vigorous agitation into an aqueous solution of ambient temperature constituted by 40.1 parts by weight of water, 5 parts by weight of ethyleneglycol and 5 parts by weight of a triethanolamine salt of a phosphoric ester of a polyarylphenol polyethoxylated on the average with 18 moles of ethylene oxide such as SOPROPHOR ® FL of Rhone-Poulenc.

The dispersion so obtained is ground in a ball mill so as to obtain a granulometry essentially less than 5 microns. Then 1 part by weight is added of a 30% emulsion of dimethylpolysiloxane such as RHODORSIL 426 ® of Rhone-Poulenc and 4 parts by weight of an aqueous dispersion containing 4% of RHODOPOL 23 ® and 0.1% of aqueous 30% formol solution.

The whitish to very light brown dispersion which results therefrom is deaerated under vacuum and filtered on a 200 microns gauze.

The flow thus obtained has the following characteristics:
appearence: homogeneous, slightly viscous white to very light brown opaque fluid (without phase separation and without sediment)
content: 400 g/l of bromoxynil equivalent, in the form of bromoxynil butyrate
density at 20° C.: 1.250
content of dry matter (105° C., 1 hour): 42%
suspensitivy according to the CIPAC method (Collaborative International Pesticide Analytical Council) MT 15.1 with water standard CIPAC, reference D, at 20° C., test sample
24.4 g after 1 hour: ≧90%
cold behaviour: flowable dispersion without crystals at −6° C.
viscosity at 20° C.: AFNOR n°4 cup: 40 s±5 s
free acidity
  expressed in mg of KOH/g: 5.25
  expressed in % of bromoxynil (in phenol form): 2.6.

The change in ageing at 54° C. is seen from the numerical data collected in Table I.

TABLE I

| Elapsed time t | appearance | viscosity (AFNOR n · 4) | acidity (in mg KOH/g) | acidity in % of free bromoxynil |
|---|---|---|---|---|
| 0 | homogeneous phase separation = 0 sediment = 0 | 40 ± 5 | 4.3 | 2.1 |
| 1 month | phase separation: very slight sediment = 0 | 60 ± 5 | 6.4 | 3.2 |
| 2 months | phase separation: slight sediment = 0 | 56 ± 5 | 6.9 | 3.4 |

It appears from these data that the hydrolysis of the butyric ester is negligible, even at 54° C.

On another sample manufactured according to the same process, the absence of hydrolysis was verified, after ageing at 54° C., by gas phase chromatography or GPC, the results being collected in Table II below.

TABLE II

| Elapsed time | Content of bromoxynil equivalent in ester form by GPC | Acidity in mg KOH/g |
|---|---|---|
| 0 | 386.4 | 5.2 |
| 1 month | 388.1 | 5.6 |

EXAMPLE 2

Procedure was in the manner indicated in Example 1 except that there were employed 39.9 parts by weight of technical grade ioxynil butyrate (melting point 118° C., content of ioxynil equivalent 78.8%) instead of the 42.8 parts by weight of bromoxynil butyrate, as well as 2 parts by weight of alkylphenol polyethoxylated on the average with 16.5 moles of ethylene oxide instead of alkylphenol at 10 moles, and 44 parts by weight of water instead of 40.1.

The flow obtained had the following characteristics:
appearence: homogeneous white to very light brown opaque slightly viscous fluid (without phase separation and without sediment)
content: 400 g/l of ioxynil equivalent, in the form of ioxynil butyrate
density at 20° C.: 1.274
content of dry matter: 41%
suspensitivy by the CIPAC method (Collaborative International Pesticide Analytical Council) MT 15.1 with CIPAC standard water, reference D, at 20° C., test sample 24.9 g after 1 hour: ≧90%
behaviour in the cold: flowable dispersion without crystals at −6° C.
viscosity at 20° C.: AFNOR n°4 cup: 40 s±5 s
free acidity:
  expressed in mg of KOH/g: 3.25
  expressed in % of ioxynil (phenol): 2.15.

The ageing experiment at 54° C. showed that the product remained in white opaque liquid form without phase separation nor sedimentation.

The absence of hydrolysis was checked by gas phase chromatography and gave the results collected in Table III below.

TABLE III

| Elapsed time | Content of ioxynil equivalent in ester form by GPC | Acidity in mg KOH/g |
|---|---|---|
| 0 | 397.4 | 3.7 |
| 21 days | 397.4 | 4.0 |

EXAMPLE 3

16.55 parts by weight of bromoxynil butyrate and 0.5 parts of polyethoxylated nonylphenol on the average with 10 moles of ethylene oxide are melted together and poured at room temperature and with vigorous stirring into a mixture comprising 69.2 parts by weight of an atrazine dispersion titrating 44.7% of atrazine and marketed by Ciba Geigy under the trademark selfsuspensible GESAPRIME, 5.75 parts by weight of water, 3 parts by weight of ethyleneglycol and 3 parts by weight of SOPROPHOR ® FL.

The dispersion so obtained is ground and as in Example 1, dimethylpolysiloxane emulsion is added as well as the thickener before deaerating and filtering.

The flow so obtained shows the following characteristics:
appearence: homogeneous, slightly viscous opaque white fluid
density at 20° C.: 1.162
viscosity at 20° C.: AFNOR n°4 cup: 45 s±5 s
content of dry matter: 45.8%
suspensitivy according to the CIPAC method (Collaborative International Pesticide Analytical Council) MT 15.1 with CIPAC standard water, reference D, at 20° C., test sample 21.8 g after 1 hour: ≧90%
cold behaviour: flowable dispersion without crystals at −5° C.
it contains 144 g/l of bromoxynil equivalent in the form of butyrate and 360 g/l of atrazine.

The ageing experiment of 14 days at 54° C. by the CIPAC MT 46 method shows that the product remains in white opaque liquid form without phase separation nor sedimentation.

EXAMPLE 4

71.5 parts by weight of a micronised dispersion (that is to say brought to a granulometry essentially below 5 microns), and stable, of diuron titrating 42.1% by weight of active material and containing as wetting agents-dispersing agents, SOPROPHOR ® FL, nonylphenol condensed with 10 moles of ethylene oxide and, as thickener, RHODOPOL ® 23, with 12.1 parts by weight of the flow of Example 1, then 13.4 parts by weight of water are added, with vigorous agitation, 3 parts by weight of an aqueous dispersion containing 4% by weight of RHODOPOL ® 23. The white dispersion which results therefrom is deaerated under vacuum and filtered on a gauze of 200 microns.

The flow so obtained has the characteristics indicated below:
appearance: homogeneous, slightly viscous opaque white fluid
density at 20° C.: 1.161
viscosity at 20° C.: AFNOR n°4 cup: 46 s
content of dry matter: 36% by weight
suspensitivy according to the CIPAC method (Collaborative International Pesticide Analytical Council) MT 15.1 with CIPAC standard water, reference D, at 20° C., test sample 27.7 g after 1 hour: ≧90%
this flow contains 45 g/l of bromoxynil equivalent in the form of butyrate and 350 g/l of diuron.

The ageing experiment carried out in the manner as indicated in Example 3 shows that the product remains in the form of an opaque white liquid showing a very slight ring.

EXAMPLE 5

Procedure was as in Example 4 but by employing this time 12.7 parts by weight of the flow of Example 1, 70.7 parts by weight of the atrazine dispersion described in Example 3 as well as 13.6 parts by weight of water and 3 parts by weight of the aqueous dispersion with 4% of thickener previously dispersed, also described in Example 4.

After deaeration and filtering identical with those of Example 4, a product having the following characteristics is obtained:
appearance: homogeneous, slightly viscous opaque white fluid
density at 20° C.: 1.107
viscosity at 20° C.: AFNOR n°4 cup: 36 s
content of dry matter: 36%
suspensitivy according to the CIPAC method (Collaborative International Pesticide Analytical Council) MT 15.1 with CIPAC standard water, reference D, at 20° C., test sample 27 g after 1 hour: ≧90%
this product contained 45 g/l of bromoxynil equivalent in the form of butyrate and 350 g/l of atrazine.

Example 5 compared with Example 3 shows that it is possible, on the one hand, to associate at will very different proportions of diverse active materials, in the event bromoxynil butyrate and atrazine and, on the other hand, to employ different operational methods since, in Example 3, the bromoxynil butyrate is micronised in the presence of the atrazine dispersion previously manufactured whereas, in Example 5, the dispersions manufactured separately are mixed.

The ageing experiment carried out in the manner as indicated in Example 3 shows that the product remains in white opaque liquid form without phase separation nor sedimentation.

EXAMPLE 6

Procedure was as in Example 5 by mixing 6.7 parts by weight of the flow of Example 1 with
25.35 parts by weight of the stable diuron dispersion described in Example 4,
47.85 parts by weight of the atrazine dispersion described in Example 3,
17.1 parts by weight of water and
3 parts by weight of the 4% aqueous dispersion of thickener described in Example 4.

After deaeration under vacuum and filtration on a gauze on 200 microns, a composition having the characteristics indicated below was obtained:
appearance: homogeneous, slightly viscous opaque white fluid
density at 20° C.: 1.125
viscosity at 20° C.: AFNOR n°4 cup: 40 s
content of active materials:
240 g/l of atrazine
120 g/l of diuron
24 g/l of bromoxynil equivalent in butyrate form.

The ageing experiment carried out in the manner as indicated in Example 3 shows that the product remains in white opaque liquid form without phase separation nor sedimentation.

EXAMPLE 7

Procedure was as in Example 6 by mixing 6.6 parts by weight of the flow of Example 1 with
23.6 parts by weight of the atrazine dispersion described in Example 3,
50.15 parts by weight of the diuron dispersion described in Example 4,
16.65 parts by weight of water and
3 parts by weight of the 4% aqueous dispersion of thickener described in Example 4.

The composition so obtained has the following characteristics:
appearance: homogeneous, opaque white liquid
density at 20° C.: 1.137
viscosity at 20° C.: AFNOR n°4 cup: 45 s
content of active materials:
120 g/l of atrazine
240 g/l of diuron
24 g/l of bromoxynil equivalent in butyrate form.

The ageing experiment carried out in the manner as indicated in Example 3 showed that the product remains in white opaque liquid form without phase separation nor sedimentation.

EXAMPLE 8

Procedure was as previously by mixing 6.7 parts by weight of the flow of Example 1 with
37.85 parts by weight of the diuron dispersion described in Example 4,
35.65 parts by weight of the atrazine dispersion described in Example 3,
16.8 parts by weight of water and
3 parts by weight of the 4% aqueous dispersion of thickener described in Example 4.

The composition so obtained had the following characteristics:
appearance: homogeneous, opaque white liquid density at 20° C.: 1.130
viscosity at 20° C.: AFNOR n°4 cup: 50 s
content of active materials:
 180 g/l of atrazine
 180 g/l of diuron
 24 g/l of bromoxynil equivalent in butyrate form.

The ageing experiment at 54° C. showed that the product remains in white opaque liquid form without phase separation nor sedimentation.

EXAMPLE 9

9.05 parts by weight of technical aminotriazole, titrating 98% were solubilized in 36.75 parts by weight of water. It was warmed as necessary up to 40° C. to accelerate solubilization.

Then there were added 8.5 parts by weight of the flow of Example 1, then 42.2 parts by weight of the diuron dispersion described in Example 4, and lastly 3.5 parts by weight of the 4% aqueous dispersion of thickener described in Example 4.

After deaeration under vacuum and filtration on a 200 microns gauze, a composition having the following characteristics was obtained:
appearence: homogeneous, opaque white liquid
density at 20° C.: 1.130
viscosity at 20° C.: AFNOR n°4 cup: 40 s
content of active materials:
 100 g/l of aminotriazole
 200 g/l of diuron
 30 g/l of bromoxynil equivalent in butyrate form.

This example confirms that it is possible to associate bromoxynil butyrate in aqueous dispersion with an aqueous solution of another active material like aminotriazole.

The ageing experiment carried out in the manner as indicated in Example 3 showed that the product presents itself fairly rapidly in opaque liquid form with considerable phase separation (about 50%).

EXAMPLE 10

Procedure was as in Example 9 by dissolving 9.45 parts by weight of aminotriazole with 98% purity in 37 parts by weight of water then by adding:

8.9 parts by weight of the flow in Example 1, 41.4 parts by weight of the atrazine dispersion described in Example 3, and lastly 3.25 parts by weight of the 4% aqueous dispersion of thickener described in Example 4.

It is deaerated under vacuum then filtered on a 200 microns gauze and the composition thus obtained had the following characteristics:
appearance: homogeneous, opaque white liquid
density at 20° C.: 1.082
viscosity at 20° C.: AFNOR n°4 cup: 35 s
content of active materials:
 100 g/l of aminotriazole
 200 g/l of atrazine
 30 g/l of bromoxynil equivalent in butyrate form.

The ageing experiment carried out in the same manner as Example 3 showed that the product remained in white opaque liquid form without phase separation nor sedimentation.

EXAMPLE 11

Procedure was as in the preceding Example by dissolving 6.95 parts by weight of aminotriazole in 31 parts by weight of water possibly warmed then by adding:

5.8 parts by weight of the flow of Example 1, 26.9 parts by weight of the diuron dispersion described in Example 4, 25.35 parts by weight of the atrazine dispersion described in Example 3, and 4 parts by weight of the 4% aqueous dispersion of thickener described in Example 4.

At the end of the operation, the characteristics of the product thus obtained were as follows:
appearence: homogeneous, opaque white liquid
density at 20° C.: 1.105
viscosity at 20° C.: AFNOR n°4 cup: 45 s
content of active materials:
 75 g/l of aminotriazole
 125 g/l of atrazine
 125 g/l of diuron
 20 g/l of bromoxynil equivalent in butyrate form.

The ageing experiment carried out in the manner as indicated in Example 3 showed that the product remained in white opaque liquid form without phase separation nor sedimentation.

EXAMPLE 12

Procedure was as in the preceding Example by dissolving 6.95 parts by weight of aminotriazole in 30.55 parts by weight of water then by adding:

5.8 parts by weight of the flow of Example 1, 18.3 parts by weight of the diuron dispersion described in Example 4, 34.4 parts by weight of the atrazine dispersion described in Example 3, and 4 parts by weight of the 4% aqueous dispersion of thickener described in Example 4.

The characteristics of the product obtained were as follows:
appearence: homogeneous, opaque white liquid
density at 20° C.: 1.107
viscosity at 20° C.: AFNOR n°4 cup: 50 s
content of active materials:
 75 g/l of aminotriazole
 170 g/l of atrazine
 85 g/l of diuron
 20 g/l of bromoxynil equivalent is butyrate form.

The ageing experiment carried out in the manner as indicated in Example 3 showed that the product remained in the form of white opaque liquid without phase separation nor sedimentation.

EXAMPLE 13

Procedure was as in the preceding Example by dissolving 6.95 parts by weight of aminotriazole in 29.55 parts by weight of water then by adding:

36.5 parts by weight of the diuron dispersion described in Example 4, 17.2 parts by weight of the atrazine dispersion described in Example 3, 5.8 parts by weight of the flow of Example 1 and 4 parts by weight of the 4% aqueous dispersion of thickener described in Example 4.

The characteristics of the product so obtained were as follows:
appearence: homogeneous, opaque white liquid
density at 20° C.: 1.108
viscosity at 20° C.: AFNOR n°4 cup: 47 s
content of active materials:
 75 g/l of aminotriazole
 85 g/l of atrazine
 170 g/l of diuron 20 g/l of bromoxynil equivalent in butyrate form.

The ageing experiment carried out in the manner as indicated in Example 3 showed that the product remained in white opaque liquid form without phase separation nor sedimentation, a very slight ring could be present.

EXAMPLE 14

12.5 parts by weight of the flow of bromoxynil butyrate of Example 1 were mixed with 69.25 parts by weight of a simazine dispersion (titrating 44.8% of simazine and marketed by Ciba Geigy under the trademark GESATOPE selfsuspendible, 15.25 parts by weight of water, 3 parts by weight of the aqueous dispersion described in Example 4.

The resulting product had the following characteristics:

appearence: homogeneous, slightly viscous, opaque white liquid
density at 20° C.: 1.128
viscosity at 20° C.: AFNOR n°4 cup: 55 s±5 s
content of active materials:
    45 g/l of bromoxynil equivalent in butyrate form 350 g/l of simazine.

The ageing experiment carried out in the manner as indicated in Example 3 showed that the product remained in white opaque liquid form without sedimentation but with possibly a slight phase separation.

EXAMPLE 15

Procedure was as in Example 8 by mixing 6.6 parts by weight of the flow of Example 1 with 37.65 parts by weight of the diuron dispersion described in Example 4, 35.35 parts by weight of the simazine dispersion described in Example 14, 17.4 parts by weight of water and 3 parts by weight of the 4% aqueous dispersion of thickener described in Example 4.

The composition so obtained had the following characteristics:

appearance: homogeneous, slightly viscous, opaque white liquid
density at 20° C.: 1.136
viscosity at 20° C.: AFNOR n°4 cup: 53 s±5 s
content of active materials:
    24 g/l of bromoxynil equivalent in butyrate form
    180 g/l of diuron
    180 g/l of simazine.

The ageing experiment carried out in the manner as in Example 3 showed that the product remained in white opaque liquid form without phase separation nor sedimentation.

EXAMPLE 16

Procedure was as in Example 8 by mixing 6.7 parts by weight of the flow of Example 1 with 25.3 parts by weight of the diuron dispersion described in Example 4, 47.5 parts by weight of the simazine dispersion described in Example 14, 17.5 parts by weight of water and 3 parts by weight of the 4% aqueous dispersion of thickener described in Example 4.

The composition so obtained had the following characteristics:

appearance: homogeneous, slightly viscous, opaque white liquid
density at 20° C.: 1.127
viscosity at 20° C.: AFNOR n°4 cup: 48 s±5 s
content of active materials:
    24 g/l of bromoxynil equivalent in butyrate form
    120 g/l of diuron
    240 g/l of simazine.

The ageing experiment carried out in the manner as indicated in Example 3 showed that the product remained in white opaque liquid form without phase separation nor sedimentation.

EXAMPLE 17

Procedure was as in Example 8 by mixing 6.6 parts by weight of the flow of Example 1 with 50.1 parts by weight of the diuron dispersion described in Example 4, 23.5 parts by weight of the simazine dispersion described in Example 14, 16.8 parts by weight of water and 3 parts by weight of the 4% aqueous dispersion of thickener described in Example 4.

The composition so obtained had the following characteristics:

appearance: homogeneous, slightly viscous, opaque white liquid
density at 20° C.: 1.139
viscosity at 20° C.: AFNOR n°4 cup: 49 s±5 s
content of active materials:
    24 g/l of bromoxynil equivalent in butyrate form
    240 g/l of diuron
    120 g/l of simazine.

The ageing experiment carried out in the manner as indicated in Example 3 showed that the product remained in white opaque liquid form without phase separation nor sedimentation.

EXAMPLE 18

Procedure was as in Example 10 by dissolving 9.2 parts by weight of aminotriazole with 98% purity in 38.95 parts by weight of water and then adding:

8.5 parts by weight of the flow of Example 1, 40.35 parts by weight of the simazine dispersion described in Example 14 and 3 parts by weight of the 4% aqueous dispersion of thickener described in Example 4.

It is deaerated under vacuum then filtered on a 200 microns gauze.

The composition so obtained had the following characteristics:

appearance: homogeneous, opaque white liquid
density at 20° C.: 1.108
viscosity at 20° C.: AFNOR n°4 cup: 32 s
content of active materials:
    30 g/l of bromoxynil equivalent in butyrate form
    100 g/l of aminotriazole
    200 g/l of simazine.

The ageing experiment carried out in the manner as indicated in Example 3 showed that the product remained in white opaque liquid form without phase separation nor sedimentation.

EXAMPLE 19

Procedure was as in Example 11 by dissolving 6.9 parts by weight of aminotriazole with 98% purity in 31.3 parts by weight of water, if necessary warmed, then adding:

5.8 parts by weight of the flow of Example 1,
26.8 parts by weight of the diuron dispersion described in Example 4,
25.2 parts by weight of the simazine dispersion described in Example 14 and
4 parts by weight of the 4% aqueous dispersion of thickener described in Example 4.

At the end of the operation, the characteristics of the product so obtained were as follows:
appearence: homogeneous, opaque white liquid
density at 20° C.: 1.109
viscosity at 20° C.: AFNOR n°4 cup: 45 s
content of active materials:
  75 g/l of aminotriazole
  125 g/l of simazine
  125 g/l of diuron
  20 g/l of bromoxynil equivalent in butyrate form.

The ageing experiment carried out in the manner as indicated in Example 3 showed that the product remained in white opaque liquid form without sedimentation but with possibly a very slight phase separation.

EXAMPLE 20

Procedure was as in Example 19 by dissolving 6.95 parts by weight of aminotriazole with 98% purity in 30.6 parts by weight of water, if necessary warmed, then adding:
5.75 parts by weight of the flow of Example 1,
18.3 parts by weight of the diuron dispersion described in Example 4,
34.4 parts by weight of the simazine dispersion described in Example 14 and
4 parts by weight of the 4% aqueous dispersion of thickener described in Example 4.

At the end of the operation, the characteristics of the product so obtained were as follows:
appearence: homogeneous, opaque white liquid
density at 20° C.: 1.105
viscosity at 20° C.: AFNOR n°4 cup: 46 s
content of active materials:
  75 g/l of aminotriazole
  170 g/l of simazine
  85 g/l of diuron
  20 g/l of bromoxynil equivalent in butyrate form.

The ageing experiment carried out in the manner as indicated in Example 3 showed that the product remained in white opaque liquid form without sedimentation but with possibly a very slight phase separation.

EXAMPLE 21

Procedure was as in Example 19 by dissolving 6.90 parts by weight of aminotriazole with 98% purity in 29.95 parts by weight of water, possibly warmed, then adding:
5.7 parts by weight of the flow of Example 1,
36.35 parts by weight of the diuron dispersion described in Example 4,
17.1 parts by weight of the simazine dispersion described in Example 14 and
4 parts by weight of the 4% aqueous dispersion of thickener described in Example 4.

At the end of the operation, the characteristics of the product so obtained were as follows:
appearence: homogeneous, opaque white liquid
density at 20° C.: 1.111
viscosity at 20° C.: AFNOR n°4 cup: 46 s
content of active materials:
  75 g/l of aminotriazole
  85 g/l of simazine
  170 g/l of diuron
  20 g/l of bromoxynil equivalent in butyrate form.

The ageing experiment carried out in the manner as indicated in Example 3 showed that the product remained in white opaque liquid form without sedimentation but with possibly a very slight phase separation.

EXAMPLE 22

21.8 parts by weight of the product of Example 2 were mixed with 78.2 parts by weight of a stable aqueous dispersion of chlortoluron titrating 43.7% by weight of the active material marketed by the Ciba Geigy Company under the trademark DICURAN self-suspensible.

The mixture is, if necessary, deaerated under vacuum and has the following characteristics:
appearance: homogeneous, opaque white liquid
density at 20° C.: 1.169
viscosity at 20° C.: AFNOR n°4 cup: 33 s
content of active materials:
  80 g/l of ioxynil equivalent in butyrate form
  400 g/l of chlortoluron.

The ageing experiment carried out in the manner as indicated Example 3 showed that the product remained in white opaque liquid form without sedimentation but with possibly a very slight phase separation.

EXAMPLE 23

22.6 parts by weight of the product of Example 2 were mixed with
77.1 parts by weight of an isoproturon aqueous dispersion titrating 45.9% by weight of active material and marketed by the Ciba Geigy Company under the trademark OFAL 500 self-suspensible, and
0.3 part by weight of water.

The mixture was, if necessary, deaerated under vacuum and had the following characteristics:
appearance: homogeneous, light beige opaque liquid
density at 20° C.: 1.130
viscosity at 20° C.: AFNOR n°4 cup: 33 s
content of active materials:
  80 g/l of ioxynil equivalent in butyrate form
  400 g/l of isoproturon.

The ageing experiment carried out in the manner as indicated Example 3 showed that the product remained in white opaque liquid form without sedimentation but with possibly a very slight phase separation.

EXAMPLE 24

45.4 parts by weight of the product of Example 1 were mixed with
46.3 parts by weight of the product of Example 2,
7.3 parts by weight of water and
1 part by weight of an aqueous dispersion containing 4% of a thickening product described in Example 4.

The mixture was, if necessary, deaerated under vacuum and had the following characteristics:
appearance: light brown opaque liquid
density at 20° C.: 1.238
viscosity at 20° C.: AFNOR n°4 cup: 42 s
content of active materials:
  180 g/l of ioxynil equivalent in butyrate form
  180 g/l of bromoxynil equivalent in butyrate form.

The ageing experiment carried out in the manner as indicated Example 3 showed that the product remained in white opaque liquid form without sedimentation but with possibly a very slight phase separation.

EXAMPLE 25

49.8 parts by weight of the product of Example 1 were mixed with 43.1 parts by weight of an aqueous dispersion of bromoxynil in phenolic form titrating 36.9% by weight of bromoxynil and manufactured by Applicant's Company under the trademark SABRE, 6.1 parts by weight of water and 1 part by weight of the aqueous dispersion containing 4% of a thickening product described in Example 4.

The mixture was, if necessary, deaerated under vacuum and had the following characteristics:
appearance: homogeneous, opaque white liquid
density at 20° C.: 1.257
viscosity at 20° C.: AFNOR n°4 cup: 45 s
content of active materials:
  400 g/l of bromoxynil equivalent of which 200 were in butyrate form.

This example showed that it was possible to have the same material in several associated forms and in any proportions.

The ageing experiment carried out in the manner as indicated Example 3 showed that the product remained in white opaque liquid form without sedimentation but with possibly a very slight phase separation.

EXAMPLE 26

Flow containing 150 g/l of bromoxynil in butyrate form and 100 g/l of dicamba in the form of diethanolamine salt which is soluble in aqueous medium.

41 parts by weight of the flow of Example 1 and 3.6 parts by weight of an aqueous dispersion containing 4% of RHODOPOL 23 ® described in Example 4 is mixed with an aqueous solution containing:

39.4 parts by weight of water,
0.9 part by weight of ethyleneglycol,
5.2 parts by weight of diethanolamine and
9.9 parts by weight of technical dicamba (content 88%) in the form of flow.

The mixture obtained is deaerated under vacuum and has the following characteristics:
appearance: homogeneous, beige opaque liquid
density at 20° C.: 1.155
viscosity at 20° C.: AFNOR n°4 cup: 40 s±5 s
content of dry matter (105° C., 1 hour): 28% by weight
suspensitivy according to the CIPAC method MT 15.1 with CIPAC water standard, reference D, at 20° C., test sample 35.7 g after 1 hour: ≧90%
cold behaviour: flowable dispersion without crystals at −5° C.
content of active materials:
  150 g/l of bromoxynil equivalent in butyrate form and
  100 g/l of dicamba in the form of diethanolamine salt.

The ageing experiment at 54° C. shows that the product remains in the form of a beige opaque liquid, without phase separation nor sedimentation.

EXAMPLE 27

Flow containing 100 g/l of bromoxynil in butyrate form and 480 g/l of metolachlore.

28.25 parts by weight of the flow of Example 1 are mixed with an aqueous dispersion containing:
45.15 parts by weight of 96% technical metolachlore in the form of flow,
24.6 parts by weight of water and
2 parts by weight of the 4% aqueous dispersion of RHODOPOL 23 ® described in Example 4.

The mixture obtained is deaerated under vacuum and has the following characteristics:
appearance: homogeneous, beige opaque liquid
density at 20° C.: 1.106
viscosity at 20° C.: AFNOR n°4 cup: 45 s±5 s
content of dry matter (105° C., 1 hour): 59% by weight
suspensitivy according to the CIPAC method MT 15.1 with CIPAC water standard, reference D, at 20° C., test sample 19 g after 1 hour: ≧85%
cold behaviour: flowable dispersion without crystals at 0° C.
content of active materials:
  100 g/l of bromoxynil equivalent in butyrate form and
  480 g/l of metolachlore.

The ageing experiment at 54° C. shows that the product remains in the form of a beige opaque liquid, without phase separation nor sedimentation.

EXAMPLE 28

Flow containing 283 g/l of metolachlore, 145 g/l of atrazine and 57 g/l of bromoxynil in butyrate form.

16.25 parts by weight of the flow of Example 1 are mixed with 83.75 parts by weight of a flow containing 15.84% of atrazine and 30.75% of metolachlore and marketed by Ciba Geigy under the trademark AUTOSUSPENSIBLE PRIMEXTRA.

The mixture obtained is deaerated under vacuum, filtered and has the following characteristics:
appearance: homogeneous, beige opaque liquid
density at 20° C.: 1.097
viscosity at 20° C.: AFNOR n°4 cup: 45 s±5 s
content of dry matter (105° C., 1 hour): 49% by weight
suspensitivy according to the CIPAC method MT 15.1 with CIPAC water standard, reference D, at 20° C., test sample 23 g after 1 hour: ≧90%
cold behaviour: flowable dispersion without crystals at −5° C.
content of active materials:
  283 g/l of metolachlore
  145 g/l of atrazine and
  57 g/l of bromoxynil equivalent in butyrate form.

The ageing experiment at 54° C. shows that the product remains in the form of a white opaque liquid, without phase separation nor sedimentation.

EXAMPLE 29

Flow containing 200 g/l of bromoxynil in butyrate form and 62.5 g/l of isoxaben.

54.5 parts by weight of the flow of Example 1 are mixed with 45.5 parts by weight of a dispersion in the form of flow titrating 12% of isoxaben and marketed by Lilly France under the trademark CENT 7.

After possible deaeration and filtration, the product obtained has the following characteristics:
appearance: homogeneous, light beige opaque liquid
density at 20° C.: 1.149
viscosity at 20° C.: AFNOR n°4 cup: 60 s±10 s
content of dry matter (105° C., 1 hour): 30%
suspensitivy according to the CIPAC method MT 15.1 with CIPAC water standard, reference D, at 20° C., test sample 33.3 g after 1 hour: ≧90%
cold behaviour: flowable dispersion without crystals at −10° C.

content of active materials:
  200 g/l of bromoxynil equivalent in butyrate form and
  62.5 g/l of isoxaben.

The ageing experiment at 54° C. shows that the product remains in the form of a beige opaque liquid, without phase separation nor sedimentation.

EXAMPLE 30

Flow containing 200 g/l of ioxynil in butyrate form and 62.5 g/l of isoxaben.

55.05 parts by weight of the flow of Example 2 are mixed with 44.95 parts by weight of the isoxaben flow described in Example 29.

After deaeration under vacuum and filtration, the product has the following characteristics:
appeareance: homogeneous, light beige opaque liquid
density at 20° C.: 1.171
viscosity at 20° C.: AFNOR n°4 cup: 60 s±10 s
content of dry matter (105° C., 1 hour): 30% by weight
suspensitivy according to the CIPAC method MT 15.1 with CIPAC water standard, reference D, at 20° C., test sample 35.7 g after 1 hour: ≧85%
cold behaviour: flowable dispersion without crystals at −10° C.
content of active materials:
  200 g/l of ioxynil equivalent in butyrate form and
  62.5 g/l of isoxaben.

The ageing experiment at 54° C. shows that the product remains in the form of a beige opaque liquid, without phase separation nor sedimentation.

EXAMPLE 31

Flow containing 400 g/l of ioxynil in acetate form.

35.5 parts by weight of technical grade ioxynil acetate (melting point 204° C., ioxynil equivalent content 88%) are mixed into a mixture constituted by:
49.8 parts by weight of water,
5 parts by weight of ethyleneglycol,
1 part by weight of nonylphenol (polyethoxylated on the average with 10 moles of ethylene oxide)
3.6 parts by weight of a mixture of alkylsulfonate and polyethoxylated vegetable oil marketed by Applicants under the trademark Galoryl DM 562 ® and
0.1 part by weight of a 30% emulsion of dimethylpolysiloxane such as RHODOSIL 426 ® marketed by Rhone-Poulenc.

The dispersion so obtained is ground in a ball mill so as to obtain a granulometry essentially less than 10 microns.

Then 5 parts by weight of an aqueous dispersion containing 4% of RHODOPOL 23 ® are added.

The whitish dispersion resulting therefrom is deaerated under vacuum and filtered on a 200 microns gauze.

The flow so obtained has the following characteristics:
appeerence: homogeneous, opaque white, slightly viscous liquid without phase separation or sedimentation
density at 20° C.: 1.28±0.01
viscosity at 20° C.: AFNOR n°4 cup: 50 s±5 s
content of dry matter (105° C., 1 hour): (36±1)% by weight
suspensitivy according to the CIPAC method MT 15.1 with CIPAC water standard, reference D, at 20° C., test sample 27.6 g after ½ hour: ≧90%
cold behaviour: flowable dispersion without crystals at −5° C.
content of active materials: 400 g/l of ioxynil in acetate form.

The ageing experiment at 54° C. shows that the product remains in the form of a homogeneous opaque white liquid, without phase separation nor sedimentation.

EXAMPLE 32

Flow containing 400 g/l of bromoxynil in acetate form.

38 parts by weight of technical grade bromoxynil acetate (melting point 154° C., bromoxynil equivalent content 85%) are mixed with:
47.3 parts by weight of water,
5 parts by weight of ethyleneglycol,
1 part by weight of nonylphenol (polyethoxylated on the average with 10 moles of ethylene oxide)
3.6 parts by weight of Galoryl DM 562 ® marketed by Applicants and
0.1 part by weight of a 30% emulsion of dimethylpolysiloxane such as RHODOSIL 426 ® marketed by Rhone-Poulenc.

The dispersion so obtained is ground in a ball mill so as to obtain a granulometry essentially less than 10 microns.

Then 5 parts by weight of an aqueous dispersion containing 4% of RHODOPOL 23 ® are added.

The whitish dispersion resulting therefrom is deaerated under vacuum and filtered on a 200 microns gauze.

The flow so obtained has the following characteristics:
appeerence: homogeneous, opaque white, slightly viscous liquid without phase separation or sedimentation
density at 20° C.: 1.24±0.01
viscosity at 20° C.: AFNOR n°4 cup: 50 s±5 s
content of dry matter (105° C., 1 hour): (38±1)% by weight
suspensitivy according to the CIPAC method MT 15.1 with CIPAC water standard, reference D, at 20° C., test sample 26.3 g after ½ hour: ≧80%
cold behaviour: flowable dispersion without crystals at −5° C.
content of active materials: 400 g/l of bromoxynil in acetate form.

The ageing experiment at 54° C. shows that the product remains in the form of a homogeneous opaque white liquid, without phase separation nor sedimentation.

EXAMPLE 33

Flow containing 200 g/l of bromoxynil in butyrate form and 66.7 g/l of clopyralide in the form of sodium salt which is soluble in aqueous medium.

17.6 parts by weight of an aqueous solution containing 400 g/l of clopyralide salt of sodium (32.6% of active ingredient "a.i" equivalent) are mixed into a mixture constituted by:
53.75 parts by weight of flow of Example 1,
4 parts by weight of a 4% dispersion of RHODOPOL 23 ®
1 part by weight of ethyleneglycol and
23.65 parts by weight of water.

After homogeneization and deaeration under vacuum, the product has the following characteristics:
appeerance: homogeneous, beige opaque liquid without phase separation or sedimentation
density at 20° C.: 1.165
viscosity at 20° C.: AFNOR n°4 cup: 46 s
content of dry matter (105° C., 1 hour): (30±1)% by weight suspensitivy according to the CIPAC method MT 15.1 with CIPAC water standard, reference D, at 20° C., test sample 43.5 g after 1 hour: ≧90%
cold behaviour: flowable dispersion without crystals at −5° C.
content of active materials:
  200 g/l of bromoxynil equivalent in butyrate form and
  66.7 g/l of clopyralide in the form of sodium salt.

The ageing experiment at 54° C. shows that the product remains in the form of a beige opaque liquid, without phase separation nor sedimentation.

EXAMPLE 34

Flow containing 200 g/l of ioxynil in butyrate form and 66.7 g/l of clopyralide in the form of sodium salt which is soluble in an aqueous medium.

17.3 parts by weight of an aqueous solution with 400 g/l of clopyralide salt of sodium (32.6% of a.i. equivalent) are mixed into a mixture constituted by:
54.4 parts by weight of flow of Example 2,
4 parts by weight of a 4% dispersion of RHODOPOL 23 ®
1.3 part by weight of ethyleneglycol and
23 parts by weight of water.

After homogeneization and deaeration under vacuum, the product has the following characteristics:
appearance: homogeneous, beige opaque liquid without phase separation or sedimentation
density at 20° C.: 1.191
viscosity at 20° C.: AFNOR n°4 cup: 35 s
content of dry matter (105° C., 1 hour): (30±1)% by weight suspensitivy according to the CIPAC method MT 15.1 with CIPAC water standard, reference D, at 20° C., test sample 44.2 g after 1 hour: ≧90%
cold behaviour: flowable dispersion without crystals at −5° C.
content of active materials:
  200 g/l of ioxynil equivalent in butyrate form and
  66.7 g/l of clopyralide in the form of sodium salt.

The ageing experiment at 54° C. shows that the product remains in the form of a beige opaque liquid, without phase separation nor sedimentation.

The herbicidal compositions according to the invention were employed on maize cultures, on straw cereals, on meadow grasses, on vegetable crops, on leguminous crops, on vineyards and orchards and as total herbicides.

The excellent selectivity of the herbicidal compositions according to the invention appears when the said compositions are used by way of the process according to the invention.

The applications were carried out by spraying of mixtures in amounts which could vary from 20 l to 1000 l of mixture/ha and, more particularly,
from 20 to 80 l of spray-mixture/ha in the case of ground applications called "low volume" or in the case of aerial applications,
from 150 to 500 l of spray-mixture/ha in the case of conventional ground applications.

It is recalled that the term "spray mixture" denotes the result of mixing a given dose of formulation with a definite amount of water, the said given dose corresponding to the overall amount of active ingredient per hectare, which amount remains constant whatever the method of application selected.

Thus, if for example there is a need to use an amount of 1 liter of commercial product per hectare, as to say, for example, of a stable dispersion or flow according to Example 1, there would be, in the case of a conventional ground application, to spray 500 l of "spray-mixture" composed of 1 l of commercial product and 499 l of water and, in the case of an aerial application, there would be sprayed 20 l of "spray-mixture" composed of 1 l of commercial product and 19 l of water.

The application is made after the sowing of the crop or after the emergence of the latter.

These applications are for the purpose of
in the case of formulations of the flow type based on oxynils alone, destroying a certain flora present and of preventing short-term reappearances thereof,
in the case of formulations of the flow type based on one or several oxynils accompanied by other active materials in the form of flow or of compatible formulation, to improve the herbicidal spectrum of oxynils in flow form employed alone for the destruction of flora present and/or to improve initial efficacy of each individual active ingredient and/or to provide a long-term effectiveness when these accompanying active ingredients have a residual action during a duration of action of one to several months.

For applications to maize crops, it is possible to use, for example, the formulations of Examples 1, 25 and 3.

The formulation of Example 1 has a better selectivity with respect to the reference formulation constituted by an emulsifiable concentrate or E.C. based on bromoxynil octanoate or bromoxynil butyrate.

The formulation of Example 25 enables the immediate effect of the ester to be cumulated with the somewhat slower effect of the bromoxynil phenol and to reduce the useful dose of active materials/ha by means of the weaker useful dose of the ester.

The formulation of Example 3 enables the immediate effect of bromoxynil butyrate to be cumulated with the short-term leaf effect and the long-term root effect of atrazine.

The formulations according to these three examples may also be applied to sorghum crops, the latter having numerous similarities with maize crops.

According to the nature of the weeds, atrazine could be replaced with simazine under the same conditions.

For the treatment of straw cereal crops, it is already known to use:
oxynil ester (ioxynil and/or bromoxynil) in the form of emulsifiable concentrates, alone or in association with phenoxy-acids,
salts of alkali or amines of oxynil alone and/or principally associated with selected substituted ureas such as isoproturon, chlortoluron, etc.

Through this fact, the formulations according to the invention based on flows of ioxynil and/or bromoxynil esters alone and/or associated with flows of substituted ureas are advantageous due to the immediate and complementary effect of the oxynils on certain plants.

Thus,
the formulation of Example 2 (ioxynil in butyrate form) can usefully complement the effect of other active materials due to the fact of its rapid action and of a different effectiveness spectrum, the whole being used as an extemporaneous mixture ("tank-mix"),
the formulation of Example 24 (ioxynil+bromoxynil in butyrate form) has the advantage of cumulating the herbicidal spectra of ioxynil and bromoxynil, this formulation being substitutable for known emulsifiable concentrates based on octanoates and octanoates-butyrates employed alone or in the form of an extemporaneous mixture with other formulations, the formulation of Example 25 (bromoxynil butyrate+-bromoxynil phenol in flow form) enables the immediate effect to the ester to be cumulated with the somewhat slower effect of the phenol and possibly to reduce the dose of active material employed with respect to that which is necessary to apply when oxynil is applied only in phenol form.

Identical formulations may be produced with ioxynil or the association ioxynil+bromoxynil (ester and phenol).

It is also possible to use the formulations of Examples 22 and 23.

With respect to the oxynil ester formulations in emulsifiable concentrates used in extemporaneous mixture with isoproturon or chlortoluron, these compositions according to the invention (particularly Examples 22 and 23) enable a ready-for-use formulation to be produced usable under the same conditions and leading to the same effects.

In the case of vegetable crops, namely crops of liliaceae or of neighbouring species such as onions, garlic, shallots and the like, it is already known to employ ioxynil octanoate emulsifiable concentrates.

With respect to these products, the formulations according to the invention and, in particular, the formulation of Example 2, enable reduction of the phytotoxicity.

For applications on vines or vineyards and orchards or as total herbicides, oxynil esters in flow formulation can advantageously be used in association with numerous active substances with a complementary action either with aminotriazole in aqueous solution to have an effect on grasses, or with substituted ureas and/or triazines to have a longer lasting effect over time.

For applications on meadow grasses and for applications on leguminous crops (peas and soya, for instance), oxynil esters in aqueous concentrated suspension could advantageously replace the oxynil esters in emulsifiable concentrate when they appear insufficiently selective for different reasons, either from varieties or from climate.

In the various preceding examples of application, the ratio of each active material can be modified so as to produce formulations adapted to each sector of use according to the nature and the age of the flora present, to the nature of the soil, to the plants in crop or to the surrounding plants and to the local climatic conditions.

It is possible to distinguish, in the case of the compositions according to the invention, between four groups.

A first group is constituted by binary formulations comprising an oxynil ester flow and a herbicide with a residual effect also in the form of a flow.

In this respect, may be mentioned the formulation of Example 5 (bromoxynil butyrate+atrazine) intended to improve the immediate performance of atrazine on adventitious flora where dicotyledons such as Amaranthus, Chenopodium and Polygonum are present and dominant.

the formulation of Example 4 (bromoxynil butyrate+-diuron) particularly intended for crops where there are present dicotyledons resistant to triazines and where the use of diuron is recommended and the formulation of Example 14 (bromoxynil butyrate+-simazine) which replaces the formulation of Example 5 for soils and varieties where atrazine prove to be phytotoxic for the crops present.

A second group is constituted by ternary formulations comprising an oxynil ester flow associated with two residual action herbicides.

In this respect may be mentioned the formulations of Examples 6, 7 and 8 (bromoxynil butyrate+atrazine+diuron), which differ from one another by the respective ratios of the different active materials and which can offer interest in the one or more cases where the association atrazine+diuron contributes to a more complete long-term effect than each active substance taken separately, the oxynil ester contributing a rapid destruction of the dicotyledons present and the formulations of Examples 15, 16 and 17 (bromoxynil butyrate+diuron+simazine) which are reserved for the cases where, according to the nature of the soils, to the varieties, to the crops or surrounding plants, the phytotoxic residual effects of the atrazine are to be feared.

A third group is constituted by ternary formulations based on oxynil ester in the form of a flow associated with a residual action herbicide and with aminotriazole in aqueous solution.

Regarding this group, may be mentioned the formulation of Example 9 (bromoxynil butyrate+-diuron+aminotriazole), the formulation of Example 10 (bromoxynil butyrate+atrazine+aminotriazole) and the formulation of Example 18 (bromoxynil butyrate+-simazine+aminotriazole).

Aminotriazole, a soluble active substance, is very much employed in vineyards, orchards and as a total weedkiller; its contribution enables a complementary and fairly rapid action to be obtained, principally on grasses but also on dicotyledons among which are those resistant to triazines.

The use rates are very variable according to the different types of utilization.

A fourth group is constituted by quaternary formulations, based on an oxynil ester in the form of a flow associated with two residual action herbicides and with aminotriazole in aqueous solution.

There may be mentioned in this respect the formulations of Examples 11, 12 and 13 (bromoxynil butyrate+atrazine+diuron+aminotriazole) and those of Examples 19, 20 and 21 (bromoxynil butyrate+-simazine+diuron+aminotriazole).

The possibilities of utilization are the same as previously.

The diversity of these non limited examples shows the possibility of resorting to oxynil esters in flow form for the production of various compositions adapted to each type of application.

The herbicidal compositions according to the invention have been the subject of tests in the glasshouse and in the open field.

Efficiency and selectivity of these compositions and formulations were examined and the results recorded were compared to those obtained with classical formulations, i.e. with aqueous concentrated suspensions of oxynil in the phenol form and with emulsifiable concentrates in the ester form; the formulations as used corresponded to what is called in the art by the expression "normes of honest and commercial products"; their utilization was satisfactory (good suspension, good emulsion when diluted) and their conservation at normal temperature was good.

The examination concerned, on the one hand, bromoxynil and, on the other hand, ioxynil, each of both active materials having different uses according to the time of utilization (autumn, winter or spring), the nature of crops and the properties of each one in relation with efficiency and phytotoxicity.

As examples, the following formulations were tested:
—as far as bromoxynil is concerned:
two formulations commercially available, the first of which is based on octanoate of bromoxynil in the form of emulsifiable concentrate (or EC, referred to by $R_1$) and the second one of which is based on bromoxynilphenol in aqueous concentrated suspension (or ACS, referred to by $R_2$), these formulations having been used on corn, sorghum, on small grains (possibly rice), on plants belonging to the family of papilionacae (leguminous crops) such as for example lucern, and on plants belonging to the family of liliacae or related plants such as garlic, onion and shallot,
one formulation of the type of emulsifiable concentrate based on butyrate (referred to $R_3$) and
one formulation based on butyrate according to the invention ($R_4$);
—as far as ioxynil is concerned:
one formulation based on octanoate in the form of emulsifiable concentrate referred to $R'_1$ (of the type of those which are normally used in the prior art),
one formulation of ioxynil in the phenol form in aqueous concentrated suspension, referred to $R'_2$ (only for sake of completeness as this formulation is not used in practice, its efficiency level being too low) in certain tests,
two formulations based on butyrate, one of which is in the form of emulsifiable concentrate whereas the other one is in the form of aqueous flow according to the invention, these two formulations being referred to respectively $R'_3$ and $R'_4$.

The formulations based on ioxynil are used on the same crops as those indicated for the formulations based on bromoxynil; rather important differences exist on the level of uses, according to the country involved, in function of the tolerance of the contemplated cultivated plants with respect to these herbicidal products in function of the local conditions proper to each technique of crop.

Hereafter, the rates of active ingredients are expressed in "equivalent oxynil phenol" (phenol equivalent) as far for the active ingredient content of the formulation as for rate per hectare.

In the following, the efficiency and the selectivity of the aqueous flows of esters of bromoxynil and of ioxynil according to the invention were tested successively and compared with those of the products of the prior art.

I. EXAMINATION OF THE PRODUCTS BASED ON BROMOXYNIL

A. Glasshouse Tests

Example 1

The phytotoxicity was tested on corn (first level of rate), the treatment being carried out at the stage of 5 leaves.

The test comprises two replicates of four plants of maize each, arranged at random in the glasshouse.

The application by conventional spraying at 0.2 MPa pressure was carried out at the rate of 500 l spray mixture per hectare.

The products referenced $R_1$, $R_2$ and $R_3$ contain respectively 240 g/l of bromoxynil in octanoate form in emulsifiable concentrate, 250 g/l of bromoxynil in phenol form in aqueous concentrated suspension and 120 g/l of bromoxynil in butyrate form in emulsifiable concentrate.

The composition according to the invention, referenced $R_4$, was based on the flow formulation according to Example 1 and contained 400 g/l of bromoxynil in butyrate form in aqueous concentrated suspension.

The rates applied and the results recorded 10 days after treatment are collected in Table IV.

TABLE IV

|  | Nature of product tested | Rate a.i. in g/ha | Phytotoxicity (in %) |
|---|---|---|---|
| $R_1$ | octanoate | 100 | 10 |
|  | 240 g/l p.e. | 200 | 10 |
|  | EC | 400 | 22.5 |
| $R_2$ | phenol | 100 | 0 |
|  | 250 g/l p.e. | 200 | 0 |
|  | ACS | 400 | 2.5 |
| $R_3$ | butyrate | 100 | 0 |
|  | 120 g/l p.e. | 200 | 30 |
|  | EC | 400 | 77 |
| $R_4$ | butyrate | 100 | 5 |
|  | 400 g/l p.e. | 200 | 5 |
|  | ACS | 400 | 10 |
|  | control |  | 0 |

Scale of phytotoxicity:
0: (control) no effect
5: acceptable
15: limit of acceptability
30: unacceptable
100: complete destruction.

It appears from the values recorded in Table IV that the formulation $R_4$ according to the invention is more selective than the emulsifiable concentrates according to the prior art.

Example 2

Examination of the phytotoxicity on corn (second level of rate); the results are those recorded 10 days after the treatment.

TABLE V

|  | Nature of product tested | Rate a.i. in g/ha | Phytotoxicity (in %) |
|---|---|---|---|
| $R_1$ | octanoate | 300 | 22.5 |
|  | 240 g/l p.e. | 600 | 40 |
|  | EC | 1200 | 90 |
| $R_3$ | butyrate | 300 | 40 |
|  | 120 g/l p.e. | 600 | 77.5 |
|  | EC | 1200 | 100 |
| $R_4$ | butyrate | 300 | 0 |
|  | 400 g/l p.e. | 600 | 10 |
|  | ACS | 1200 | 30 |
|  | control |  | 0 |

The values recorded in Table V show that for the same rate (hectare of equivalent bromoxynil), the selectivity of the flow $R_4$ according to the invention is clearly higher.

Example 3

The phytotoxicity of the same products was determined successively 5 days*, then 10 days** after the treatment of wheat crops (at the stage of 3 leaves or 3 L), barley (stage of 3 leaves), of carrot (stage of 3 leaves), of peas (stage of 3 leaves), of flax (stage 10 cm), of soya (stage of 5 leaves or 5 L) and of French bean (stage 1 leaf or 1 L), the results being recorded in Table VI.

TABLE VI

| Nature of product tested | Rate/ha g a.i. | Number of days after treatment | Wheat 3 F | Barley 3 F | Carrot 3 F | Peas 3 F | Flax 10 cm | Soya 5 F | Bean 1 F |
|---|---|---|---|---|---|---|---|---|---|
| $R_1$ octanoate 240 g/l p.e. EC | 100 | 5 | 30 */** | 22.5 / | 15 / | 30 / | 5 / | 0 / | 85 / |
|  |  | 10 | 5 | 5 | 70 | 32 | 2.5 | 0 | 85 |
|  | 200 | 5 | 30 / | 22.5 / | 70 / | 30 / | 50 / | 5 / | 95 / |
|  |  | 10 | 5 | 5 | 90 | 30 | 72 | 0 | 95 |
| $R_2$ phenol 250 g/l p.e. ACS | 100 | 5 | 0 / | 0 / | 22.5 / | 0 / | 40 / | 0 / | 15 / |
|  |  | 10 | 5 | 5 | 70 | 5 | 85 | 0 | 50 |
|  | 200 | 5 | 0 / | 0 / | 60 / | 0 / | 50 / | 5 / | 30 / |
|  |  | 10 | 5 | 5 | 85 | 5 | 90 | 0 | 60 |
| $R_3$ butyrate 120 g/l p.e. EC | 100 | 5 | 2.5 / | 2.5 / | 16 / | 0 / | 5 / | 0 / | 15 / |
|  |  | 10 | 5 | 5 | 50 | 5 | 5 | 0 | 10 |
|  | 200 | 5 | 2.5 / | 2.5 / | 50 / | 0 / | 22 / | 30 / | 30 / |
|  |  | 10 | 5 | 5 | 75 | 10 | 22 | 0 | 30 |
| $R_4$ butyrate 400 g/l p.e. ACS | 100 | 5 | 0 / | 0 / | 2.5 / | 0 / | 10 / | 0 / | 2.5 / |
|  |  | 10 | 5 | 5 | 3.5 | 3.5 | 30 | 0 | 0 |
|  | 200 | 5 | 0 / | 0 / | 15 / | 0 / | 10 / | 0 / | 2.5 / |
|  |  | 10 | 5 | 5 | 32 | 15 | 20 | 0 | 5 |

It appears from Table VI that the flow $R_4$ according to the invention is widely the less phytotoxic.

Moreover, it appears that there exists important differences from the point of view of phytotoxicity towards the different crops, namely carrots and French beans.

The flow based on bromoxynil in butyrate form according to the invention is consequently, at equal rate of phenol equivalent per hectare, distinctly less aggressive than the products of the prior art.

With regard to the latter, greater crop injury is again to be found, in the present case, to the emulsifiable concentrate based on bromoxynil octanoate compared to the emulsifiable concentrate based on bromoxynil butyrate.

B—Tests in the open field on maize crops

These tests were carried out on three varieties of maize much cultivated in France named: DEA, SABRINA, EVA.

The treatments were made post-emergence at the 2 to 8 leaves stages to appreciate:
the effectiveness and
the crop injury.

Eleven locations were taken, representing 11 different fields, of which 4 were in the north of France, 5 in the south-east and 2 in the south-west.

In each location, the products were applied twice (2 replicates) on elementary plots of land, each being 5 m in width and 10 m in length.

The treatments were realized by conventional spraying at a pressure of 0.2 MPa on the basis of 500 l of spray mixture per hectare, as in the tests in the glasshouse.

The above-said reference product $R_1$ and, by way of herbicidal composition according to the invention, the stable dispersion or flow of Example 1 (reference $R_4$), the content being 400 g/l of bromoxynil in butyrate form, were tested.

The rates (expressed as phenol bromoxynil equivalent) employed were:

TABLE VII

| Ref. No. | Nature of product tested | Rate/ha in equivalent bromoxynil phenol (g) |
|---|---|---|
| $R_1$ | octanoate 240 g/l p.e. EC | 240 336 480 |
| $R_4$ | butyrate 400 g/l p.e. ACS | 348 400 600 |

The rate as used can be adapted according to the geographical places, the nature and the vegetative stage of the weeds which are present, the varieties and the vegetative stage of corn; the rates as selected correspond to variations which can be normal in practice.

As far as product $R_4$ according to the invention is concerned, the selection of the rate was made taking into consideration the possibility that this product might be less efficient.

The rate of 336 g/ha of the emulsifiable concentrate based on octanoate was the rate considered as useful and necessary and recommended in the majority of cases in France.

This use rate may be adapted according to the geographical sites, the nature and the vegetative state of the weeds present, the varieties and the vegetative state of the maize.

The experimental fields were selected so as to include a flora for which the use of the bromoxynil emulsifiable concentrate in octanoic ester form may normally be recommended in maize crops.

The target weeds for this type of treatment are various dicotyledons (of which certain are resistant to triazines) at young stages before flowering such as Amaranthus, Atriplex, Chenopodium, Solanum, Polygonum, Matricaria, Sinapis, Raphanus, Convolvulus, but also plants such as Equisetum sp.

The results of 22 observations carried out on the average 15 days (actually, 14 to 18 days) after treatment on 11 sites, are collected in Table VIII.

There has first been studied the general effectiveness (Table VIII).

This effectiveness of action on the weeds is evaluated as follows, (knowing that 0 corresponds to a nil effectiveness and 100 to total destruction)
≧97.5%: perfect
95%: good
85%: limit of acceptability
≦70%: unacceptable.

TABLE VIII after treatment (actually 14 to 18 days) are collected in Table IX.

The markings relating to phytotoxicity (0=nil effect, 100=killed plants) are as follows:
0 to 2.5%: phytotoxicity nil or considered as nil
5%: phytotoxicity acceptable
15%: phytotoxicity at the limit of acceptability
30%: phytotoxicity unacceptable visually but the crop may be able to recover
50%: phytotoxicity unacceptable since the possibility of recovery of the crop is practically nil.

TABLE IX

| | | | PHYTOTOXICITY | | | | | |
|---|---|---|---|---|---|---|---|---|
| | Rates | | Average | Frequency of marks, in %*** | | | | |
| | | | | 0 to 15% | | | | |
| Products tested | Product l/ha | a.i. g/ha | in % ** | 0 to 2.5% | 5% | 15% | > to 15% 30% | 50% |
| R₁ EC | 1 | 240 | 6.4 | 63.6 | 9.0 | 18.1 | 9 | |
| | 1.4* | 336* | 12.2 | 40.9 | 18.1 | 13.6 | 22.7 | 4.5 |
| | 2 | 480 | 15.1 | 31.8 | 18.1 | 18.1 | 22.7 | 9 |
| R₄ flow according to Ex. 1 | 0.87 | 348 | 2.6 | 68.1 | 27.2 | 4.5 | — | — |
| | 1 | 400 | 3.1 | 77.2 | 18.1 | — | 4.5 | — |
| | 1.5 | 600 | 5.4 | 72.7 | 18.1 | — | 9 | — |

*Rate recommended by professionals
**Average of % phytotoxicity on 22 observations
***There is indicated for each formulation and each rate the percentage of "perfect", "good", etc. marks.

| | | EFFICACY | | | | | |
|---|---|---|---|---|---|---|---|
| Products tested | Rates Product l/ha | a.i. g/ha | Average in % ** | Frequency of marks in %*** | | | |
| | | | | 97.5 to 100% | 95% | 85% | ≦70% |
| R₁ EC | 1 | 240 | 86.1 | 59 | 13.6 | 22.7 | 4.5 |
| | 1.4* | 336* | 94.7 | 68.1 | 13.6 | 9 | 9 |
| | 2 | 480 | 97.2 | 81.8 | 9 | 9 | |
| R₄ flow according to Ex. 1 | 0.87 | 348 | 98 | 72.7 | 22.7 | 4.5 | |
| | 1 | 400 | 97 | 72.7 | 13.6 | 13.6 | |
| | 1.5 | 600 | 98.4 | 86.3 | 9 | 4.5 | |

*Rate recommended by professionals
**Average of % effectiveness on 22 observations
***There is indicated for each formulation and each rate the percentage of "perfect", "good", etc. marks.

Examination of these results shows that the formulation of the invention, at the rate of 348 g/ha of equivalent bromoxynil, gives an effectiveness very close to that of the reference product at the rate of 1.4 l/ha, i.e. 336 g/ha a.i., rate recommended by professionals as being the useful and necessary rate for the majority of cases.

It is noted in addition, with respect to column "≦70%" that, for the rates of 1 and 1.4 l/ha, the reference product leads to a more unequal effectiveness than the product according to the invention which therefore gives more homogeneous results.

The phytotoxicity is afterwards studied.

It is here that the superiority of the formulations according to the invention appears to its full extent, confirming the results already noted at the end of the glasshouse tests.

The results of 22 observations carried out on the above-said 11 sites and relating to phytotoxicity, expressed in % of effect on foliage on the average 15 days The results collected in Table IX lead to the following observations.

On the one hand, the average of the % of phytotoxicity confirms that the product according to the invention is distinctly less phytotoxic at all the rates studied than the reference product.

On the other hand, examination of the frequency of the phytotoxicity marks shows that, unexpectedly in the case of the product according to the invention, these marks are grouped very close to 100% in the columns corresponding to a phytotoxicity which is nil or acceptable; the superiority of the product according to the invention is seen very particularly from comparison of the marks recorded for the recommended rate of 1.4 l/ha of the reference product and from those recorded from the comparable rate, i.e. that of 0.87 l/ha of the product of Example 1.

There has also been studied, within the scope of the tests in open field, the sensitivity of the weeds. Three examples have been taken, namely Amaranthus retroflexus, Chenopodium album and Solanum nigrum, i.e. the only weeds showing considerable infestation (more than 100 plants per m²) in the 11 sites selected.

The observations were carried out at the same times as above.

The sensitivity is expressed in % sensitivity, according to the following scale:
VS: very sensitive corresponding to a destruction ≧95%
S: sensitive corresponding to a destruction <95% and ≧85%
MS: medium sensitivity corresponding to a destruction <85% and ≧70%
MR-R: medium resistance to resistant corresponding to a destruction ≦70%.

The results are collected in Table X.

TABLE X

| Product tested | Rates Product l/ha | a.i. g/ha | Amaranthus retroflexus (4**) | | | | Chenopodium album (20**) | | | | Solanum nigrum (20**) | | | |
|---|---|---|---|---|---|---|---|---|---|---|---|---|---|---|
| | | | VS | S | MS | MR-R | VS | S | MS | MR-R | VS | S | MS | MR-R |
| R₁ EC | 1 | 240 | — | 100 | — | — | 78 | 11 | 6 | 6 | 83 | 6 | 6 | 6 |
| | 1.4* | 336* | 100 | — | — | — | 83 | 6 | 11 | — | 83 | 11 | 6 | — |
| | 2 | 480 | 100 | — | — | — | 94 | 6 | — | — | 89 | — | 6 | 6 |
| R₄ flow according to Ex. 1 | 0.87 | 348 | 100 | — | — | — | 94 | 6 | — | — | 89 | — | — | 11 |
| | 1 | 400 | 50 | 50 | — | — | 94 | 6 | — | — | 89 | — | 11 | — |
| | 1.5 | 600 | 100 | — | — | — | 100 | — | — | — | 89 | — | — | 11 |

*Rate recommended
**Number of observations concerning the case where the plant is present in the test plots with respect to the total of the 22 observations Examination of the results of the tests collected in Table X shows that
on Amaranthus, the two products are practically identical,
on Chenopodium, the product according to the invention is superior,
on Solanum, the effectiveness is very close but incomplete, the low proportion of poor results being due to the fact that, on one of the sites, there were encountered plants which were too far developed during the treatment, whence lesser sensitivity.

The formulation according to the invention (flow according to example 1) shows then at the rate of 348 g/ha of equivalent bromoxynil, a phytotoxicity clearly lower than that of the formulation referred to R₁ in the form of emulsifiable concentrate used at the rate of 336 g/ha of equivalent bromoxynil, while having an overall efficiency close or even slightly higher as well as an activity slightly higher on certain important weeds.

II. EXAMINATION OF PRODUCTS BASED ON IONXYNIL

A. Glasshouse Tests

The products referenced R'₁, R'₂ and R'₃ which were employed, contain respectively 240 g/l of ioxynil in octanoate form in emulsifiable concentrate, 250 g/l of ioxynil in phenol form in aqueous concentrated suspension and 120 g/l of ioxynil in butyrate form in emulsifiable concentrate.

The composition according to the invention, referenced R'₄, was based on the flow according to Example 2 and contained 400 g/l of ioxynil in butyrate form in aqueous concentrated suspension.

In Table XI, are recorded the results obtained 15 days after the treatment, these results representing the efficiency on weeds (Amaranthus, Chenopodium, Solanum and Matricaria) treated at the stage of 3 leaves.

TABLE XI

| Nature of product tested | | Rate/ha g a.i. | Efficacy on weeds | | | |
|---|---|---|---|---|---|---|
| | | | Amaranthus | Chenopodium | Solanum | Matricaria |
| R'₁ | octanoate | 100 | 99 | 95 | 70 | 12 |
| | 240 g/l p.e. | 200 | 100 | 98 | 75 | 25 |
| | EC | 400 | | | | |
| R'₂ | phenol | 100 | 98 | 17 | 50 | 35 |
| | 250 g/l p.e. | 200 | 100 | 30 | 70 | 55 |
| | ACS | 400 | 100 | 85 | 98 | 97 |
| R'₄ | butyrate | 100 | 98 | 36 | 80 | 12 |
| | 400 g/l p.e. | 200 | 100 | 90 | 100 | 30 |
| | ACS | 400 | 100 | 100 | 100 | 80 |

It is noticed that product R'₄ according to the invention is
more efficient than R'₁ and R'₂ on Solanum,
slightly inferior on Matricaria with respect to product R'₁,
inferior with respect to R'₁ on Chenopodium.

In Table XII, are recorded the results obtained 20 days after the treatment and representing the sensitivity of the cereal crops treated on the stage of 3 leaves.

TABLE XII

| Nature of product tested | | Rate/ha g a.i. | Phytotoxicity on | | |
|---|---|---|---|---|---|
| | | | wheat Festival | wheat Arminda | barley Igri |
| R'₁ | octanoate | 100 | 2.5 | 0 | 0 |
| | 240 g/l p.e. | 200 | 7.5 | 0 | 5 |
| | EC | 400 | 7.5 | 0 | 15 |
| R'₂ | phenol | 100 | 0 | 2.5 | 0 |
| | 250 g/l p.e. | 200 | 10 | 10 | 15 |
| | ACS | 400 | 10 | 15 | 22.5 |
| R'₄ | butyrate | 100 | 0 | 0 | 0 |
| | 400 g/l p.e. | 200 | 2.5 | 0 | 0 |
| | ACS | 400 | 2.5 | 2.5 | 5 |

It appears, from the examination of these results, that product R'₄ according to the invention is less agressive than product R'₁ on wheat of the kind "Festival" and of barley of the kind "Igri".

In Table XIII, are recorded the results obtained 20 days after the treatment and representing the sensitivity of the cereal crops treated at the stage of 3 leaves with a combination of the products R'₁, R'₂ and R'₄ with isoproturon.

As far as R'₁ is concerned, the combination is a combination normally used on cereal crops to obtain the effect of ioxynil on dicotyledonous weeds and the effect of isoproturon on grasses and some dicots together, isoproturon being used at a constant rate of 1000 g/ha.

TABLE XIII

| Nature of | Phytotoxicity on | | |
|---|---|---|---|
| product tested | Rate/ha g a.i. | wheat Festival | wheat Arminda | barley Igri |
| R'₁ + isoproturon EC | 100 + 1000 | 22.5 | 22.5 | 60 |
| | 200 + 1000 | 18.5 | 30 | 80 |

TABLE XIII-continued

| Nature of product tested | | Rate/ha g a.i. | Phytotoxicity on | | |
|---|---|---|---|---|---|
| | | | wheat Festival | wheat Arminda | barley Igri |
| R'₂ ACS | + isoproturon | 400 + 1000 | 22.5 | 40 | 97 |
| | | 100 + 1000 | 22.5 | 15 | 60 |
| | | 200 + 1000 | 20 | 40 | 67 |
| | | 400 + 1000 | 50 | 60 | 100 |
| R'₄ ACS | + isoproturon | 100 + 1000 | 2.5 | 50 | 10 |
| | | 200 + 1000 | 5 | 50 | 22.5 |
| | | 400 + 1000 | 10 | 60 | 60 |

The product referred to R'₂, ACS, based on ioxynil in the phenol form is of little efficiency (low averages, no efficiency higher than 70%).

The products containing butyrate R'₃ (EC) and R'₄ (ACS) are better than the formulation R'₁ (EC based of octanoate).

The formulation R'₄ is very close but slightly weaker than formulation R'₃.

Then, was studied the sensitivity of the weeds with respect to the above-mentioned products.

The results, expressed in %, of the various sensitivity classifications are recorded in Table XV.

TABLE XV

| Nature of Product | | Rate a.i. g/ha ** | Papaver rhoeas (12 marks) | | | | Veronica hederifolia (18 marks) | | | | Stellaria media (6 marks) | | | |
|---|---|---|---|---|---|---|---|---|---|---|---|---|---|---|
| | | | VS | S | MS | MR-R | VS | S | MS | MR-R | VS | S | MS | MR-R |
| R'₁ | octanoate | 314 | 41.6 | 8.3 | 25 | 25 | 39 | 5.5 | 38.8 | 22.2 | 66.6 | 0 | 16.6 | 16.6 |
| | 240 g/l p.e. | *420 | 50 | 8.3 | 25 | 16.6 | 44.4 | 16.6 | 16.6 | 22.2 | 33.3 | 33.3 | 16.6 | 16.6 |
| | EC | 628 | 58.3 | 8.3 | 33.3 | 0 | 44.4 | 16.6 | 33.3 | 5.5 | 50 | 16.6 | 16.6 | 16.6 |
| R'₂ | phenol | 314 | 16.6 | 0 | 8.3 | 75 | 11.1 | 0 | 11.1 | 77.7 | 0 | 0 | 16.6 | 83.3 |
| | 250 g/l p.e. | 420 | 16.6 | 8.3 | 25 | 50 | 11.1 | 5.5 | 33.3 | 50 | 0 | 0 | 16.6 | 83.3 |
| | ASC | 628 | 33.3 | 16.6 | 33.3 | 16.6 | 11.1 | 5.5 | 44.4 | 38.8 | 0 | 0 | 16.6 | 83.3 |
| R'₃ | butyrate | 314 | 75 | 25 | 0 | 0 | 16.6 | 44.4 | 22.2 | 16.6 | 50 | 16.6 | 16.6 | 16.6 |
| | 120 g/l p.e. | 420 | 91.6 | 8.3 | 0 | 0 | 33.3 | 27.7 | 38.8 | 0 | 33.3 | 50 | 16.6 | 0 |
| | EC | 628 | 100 | | | | 55.5 | 22.2 | 22.2 | - 0 | 66.6 | 16.6 | 16.6 | 0 |
| R'₄ | butyrate | 314 | 66.6 | 33.3 | 0 | 0 | 33.3 | 27.7 | 27.7 | 11.8 | 33.3 | 16.6 | 33.3 | 16.6 |
| | 400 g/l p.e. | 420 | 100 | 0 | 0 | 0 | 44.4 | 27.7 | 16.6 | 11.8 | 66.6 | 16.6 | 16.6 | 0 |
| | ASC | 628 | 100 | 0 | 0 | 0 | 55.5 | 11.1 | 33.3 | 0 | 83.3 | 0 | 16.6 | 0 |

*Rate registered
**Rate/ha in bromoxynil equivalent

It appears, from these results, that the product R'₄ combined with isoproturon shows a better selectivity than the two products R'₁ and R'₂ on wheat of the kine "Festival" and on barley of the kind "Igri".

B. Tests in the open field on small grains

First of all, was tested the efficiency of products R'₁ to R'₄ on a composite flora, certain of these plants being resistant to ioxynil.

The treatment was carried out according to the manner indicated with respect to the products based on bromoxynil.

The global notes obtained are weak due to the presence of the said resistant flora.

In order to obtain better results, it is necessary to add other compounds having a complementary spectrum in order to try to obtain a destruction which is as complete as possible.

In Table XIV, are recorded the results (10 locations and 20 notes) obtained, on the one hand, 20 days* and, on the other hand, 40 days** after the treatment.

Concerning the three plants tested, it is possible to make an interesting comparison with respect to the products tested.

The product R'₂ shows a very weak activity without practical interest when used alone.

The products R'₃ and R'₄ show an activity higher than that of formulation R'₁.

That difference is very clear on Papaver, clear on Veronica and Stellaria.

There is not very marked difference between the two products R'₃ and R'₄.

From the preceding results, it appears that product R'₄ as well as product R'₃ shows the particularity with respect to formulation R'₁ of having a better efficiency on certain plants; that better efficiency provides a percentage of destruction which is more important for example on Papaver, fact which is important and new, as well as a better regularity on the plants which are present, the reactions for example on Papaver, Veronica and Stellaria being clearly closer.

From a point of view still more general, the products according to the invention and namely those based on

TABLE XIV

| Nature of product | | Rate/ha g a.i. | Percentage destruction * ** | Frequency of marks | | | |
|---|---|---|---|---|---|---|---|
| | | | | ≧97.5 * ** | 95 | 85 | ≦70 |
| R'₁ | octanoate | 314 | 56.7/57.2 | 0/0 | 5/5 | 10/15 | 85/80 |
| | 240 g/l p.e. | 420 | 65.5/64.7 | 0/10 | 0/10 | 15/10 | 85/70 |
| | EC | 600 | 71.8/71.9 | 0/20 | 15/10 | 15/5 | 70/65 |
| R'₂ | phenol | 314 | 28.8/24.6 | 0/0 | 0/0 | 0/0 | 100/100 |
| | 250 g/l p.e. | 420 | 27.3/34.1 | 0/0 | 0/0 | 0/0 | 100/100 |
| | ACS | 600 | 41.2/43 | 0/0 | 0/0 | 0/15 | 100/85 |
| R'₃ | butyrate | 314 | 67.1/67.1 | 5/5 | 10/20 | 15/10 | 70/65 |
| | 120 g/l p.e. | 420 | 69.8/71.5 | 15/30 | 16/5 | 0/10 | 70/55 |
| | EC | 600 | 74/79.9 | 10/30 | 10/5 | 25/10 | 55/55 |
| R'₄ | butyrate | 314 | 56.5/63.2 | 0/0 | 5/5 | 20/25 | 75/70 |
| | 400 g/l p.e. | 420 | 60.8/72.7 | 5/10 | 5/5 | 15/25 | 75/40 |
| | ACS | 600 | 73/80.5 | 15/25 | 5/10 | 25/20 | 55/45 | butyrate, show an efficiency clearly higher at the same rate of equivalent bromoxynil than that of the flows based on oxynil phenol and close to that of the classical formulations in the form of emulsifiable concentrates on the basis of esters, especially octanoate; furthermore, they show, in numerous tests, a better selectivity (crop tolerance) on crops where very often, according to the agronomical conditions of each test, the selectivity of the products which are known is weak and close to the limit of acceptability at the efficient rates.

The above-mentioned weak selectivity of the known products is often noticed:
on numerous grasses: meadow or ornemental grasses or cereal crops such as corn and sorghum and rice, but also on certain straw cereals such as wheat, barley, oat, triticale,
on various crops such as those of the family of papilionaceae such as for example lucern or certain vegetable crops such as for example peas,
on crops of the family of liliaceae or related such as onion, leek, garlic, shallot.

The products according to the invention authorize herbicidal treatments at rates which are close to those used for the emulsifiable concentrates, the said products improving with respect to the known products in very numerous cases, the selectivity on numerous crops where the selectivity is often weak when the emulsifiable concentrates are used.

We claim:

1. Aqueous or aqueous dispersion, stable up to two years, of at least one ester of at least one of the herbicides of the group consisting of ioxynil and bromoxynil in the solid state of a granulometry substantially less than about 5 μm, said at least one ester having a melting point higher than 65° C. and being selected from the group consisting of technical grade acetate, propionate, butyrate, isobutyrate and pivalate of bromoxynil and technical grade acetate, propionate, butyrate, isobutyrate and pivalate of ioxynil.

2. Herbicidal composition comprising an aqueous or aqueous alcoholic dispersion, stable up to two years, of at least one ester of at least one of the herbicides of the group consisting of ioxynil and bromoxynil in the solid state of a granulometry substantially less than about 5 μm, said at least one ester having a melting point higher than 65° C. and being selected from the group consisting of technical grade acetate, propionate, butyrate, isobutyrate and pivalate of bromoxynil and technical grade acetate, propionate, butyrate, isobutyrate and pivalate of ioxynil.

3. Aqueous or aqueous alcoholic dispersion according to claim 1, further comprising at least one member selected from the group consisting of surface active agents, dispersants, thickening products and protective colloids.

4. Herbicidal composition according to claim 2, further comprising at least one member selected from the group consisting of surface active agents, dispersants, thickening products and protective colloids.

5. Herbicidal composition according to claim 2, wherein the overall content of herbicide is at most 600 g/l.

6. Herbicidal composition according to claim 2 in the form of a sprayable mixture useful for application to crops.

7. Use of the herbicidal composition according to claim 2 as a total herbicide for the treatment of crops of the group consisting of maize or corn, vineyards and orchards, straw cereals, meadow grasses, vegetable crops and leguminous crops.

8. Process for the selective herbicidal treatment of crops of the group comprising corn, vineyards and orchards, straw cereals, meadow grasses, vegetable crops and leguminous crops, comprising applying a herbicidally effective amount of the herbicidal composition according to claim 2 to said crops.

9. Process according to claim 8, wherein said herbicidal composition is applied to the crops by spraying a sprayable mixture of said herbicidal composition on said crops in an amount from 20 l to 1000 l sprayable mixture/ha.

10. Process according to claim 9 wherein from 20 l to 80 l of sprayable mixture/ha is sprayed on said crops.

11. Process according to claim 9 wherein from 150 l to 500 l of sprayable mixture/ha is sprayed on said corps.

* * * * *

UNITED STATES PATENT AND TRADEMARK OFFICE
CERTIFICATE OF CORRECTION

| | | |
|---|---|---|
| PATENT NO. | : | 5,021,083 |
| DATED | : | June 4, 1991 |
| INVENTOR(S) | : | Joseph Schapira et al. |

It is certified that error appears in the above-identified patent and that said Letters Patent is hereby corrected as shown below:

Claim 1, at col. 33, line 30, after "aqueous" (second occurrence) insert --alcoholic--.

Signed and Sealed this

First Day of February, 1994

Attest:

BRUCE LEHMAN

*Attesting Officer*     Commissioner of Patents and Trademarks